US00PP26153P2

(12) United States Plant Patent
Williams

(10) Patent No.: US PP26,153 P2
(45) Date of Patent: Nov. 24, 2015

(54) ***COLOCASIA* PLANT NAMED 'ELECTRIC BLUE GECKO'**

(50) Latin Name: ***Colocasia* hybrid**
Varietal Denomination: Electric Blue Gecko

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 101 days.

(21) Appl. No.: 13/987,221

(22) Filed: Jul. 12, 2013

(51) Int. Cl.
*A01H 5/00* (2006.01)

(52) U.S. Cl.
USPC ..... Plt./373

(58) Field of Classification Search
USPC ..... Plt./373
CPC ..... A01H 5/00; A01H 5/12
See application file for complete search history.

(56) References Cited

PUBLICATIONS

Plants Nouveau, retrieved from internet Dec. 5, 2014.*

* cited by examiner

*Primary Examiner* — Keith Robinson
(74) *Attorney, Agent, or Firm* — Penny J. Aguirre

(57) ABSTRACT

A new cultivar of *Colocasia* plant named 'Electric Blue Gecko', that is characterized by its leaves that are very dark black in color with a metallic blue sheen on the upper surface and dark maroon on the lower surface, its dwarf and compact plant habit, its petioles that are dark maroon in color, and its clump forming growth habit.

2 Drawing Sheets

Botanical classification: *Colocasia* hybrid.
Cultivar designation: 'Electric Blue Gecko'.

BACKGROUND OF THE INVENTION

The present invention, *Colocasia* 'Electric Blue Gecko', relates to a new and distinct interspecific hybrid of *Colocasia*, hereinafter referred to by its cultivar name, 'Electric Blue Gecko'. 'Electric Blue Gecko' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Electric Blue Gecko' arose from a cross made in June 2010 between unnamed plants of *Colocasia* of hybrid origin from the Inventor's breeding program as the female and male parents. 'Electric Blue Gecko' was selected as a single unique plant in June of 2012 from amongst the seedlings derived from the above cross.

Asexual propagation of the new cultivar was first accomplished by in vitro propagation under the direction of the Inventor in Eustis, Fla. in July of 2012. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Electric Blue Gecko' as a new and unique cultivar of *Colocasia*.

1. 'Electric Blue Gecko' exhibits leaves that are very dark black in color with a metallic blue sheen on the upper surface and dark maroon on the lower surface.
2. 'Electric Blue Gecko' exhibits a compact and dwarf plant habit; reaching 0.9 to 12 m (3 to 4 ft) in height.
3. 'Electric Blue Gecko' exhibits petioles that are dark maroon in color.
4. 'Electric Blue Gecko' exhibits a clump forming growth habit (lacking stolons).

The female parent of 'Electric Blue Gecko', an unnamed plant of *Colocasia* of hybrid origin, differs from 'Electric Blue Gecko' in being taller in height, in having dark brown leaves with a clear sheen, in having petioles that are brown-black in color, and in producing stolons. The male parent of 'Electric Blue Gecko', an unnamed plant of *Colocasia* of hybrid origin, differs from 'Electric Blue Gecko' in having leaves that are dark blue-green in color on the upper and lower surface and in having petioles that are black in color. 'Electric Blue Gecko' can be most closely compared to *Colocasia* cultivars 'Black Magic' (not patented) and 'Mojito' (U.S. Plant Pat. No. 21,995). Both are similar to 'Electric Blue Gecko' in having large leaves that have dark coloration. 'Black Magic' differs from 'Electric Blue Gecko' in being taller in height and in having leaves that are black but lacking a metallic sheen on the upper surface and grey on the lower surface. 'Mojito' differs from 'Electric Blue Gecko' in being taller in height and in having leaves and petioles that are variegated (green with black mottling).

BRIEF DESCRIPTION OF THE DRAWINGS

The accompanying colored photographs illustrate the overall appearance and distinct characteristics of the new *Colo-*

*casia*, 'Electric Blue Gecko'. The photographs were taken of plants about 2 years in age as grown outdoors under 6 mm poly and natural lighting in Louisville, Ky. and planted in a trial garden.

Figure 1:
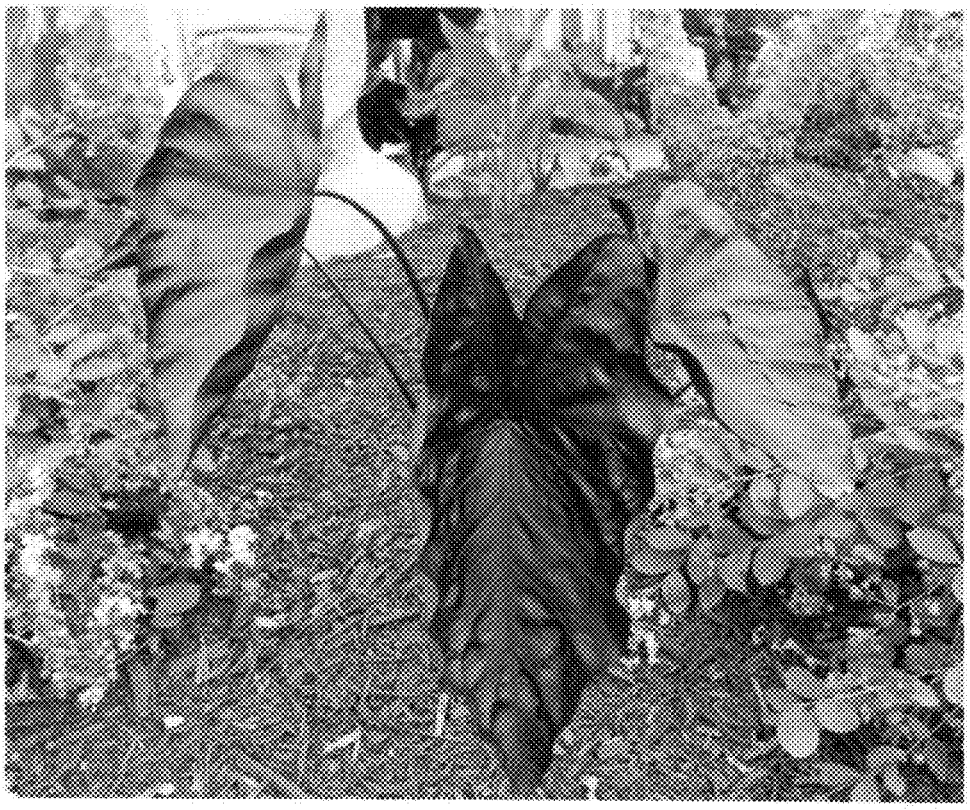
FIG. 1 provides an overall view of the foliage, petioles and plant habit of 'Electric Blue Gecko'.
Figure 2:
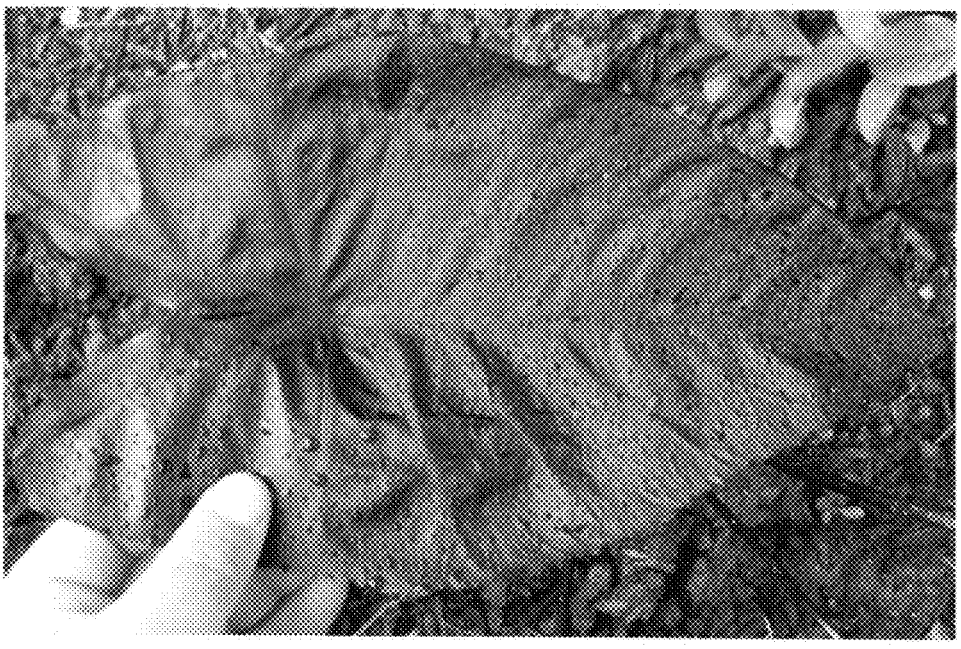

The photograph in FIG. 2 provides a close-up view of the upper surface of a leaf of 'Electric Blue Gecko'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of three year-old plants of the new cultivar as grown outdoors in a garden under full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Tropical perennial.

*Plant habit*.—Dwarf, compact, clump forming.

*Height and spread*.—Reaches 0.9 to 1.2 m (3 to 4 ft) in height and 0.6 to 0.9 m (2 to 3 ft) in spread.

*Cold hardiness*.—At least to U.S.D.A. Zone 7.

*Diseases and pests*.—No particular resistance or susceptibility has been shown to diseases and pests.

*Roots*.—Fleshy, produced in a compact mass, no stolons produced, 187C in color with growing tips 155C.

*Root development*.—Tissue culture plugs will fully root in a one-gallon container in 2 to 3 months with sufficient heat and sun.

*Corm*.—Pear-shaped, an average of 2.0 cm in diameter, 165A in color.

*Propagation type*.—In vitro propagation is preferred.

*Growth rate*.—Moderate.

*Stem description*.—Stemless.

Foliage description:

*Leaf shape*.—Lanceolate to oblanceolate.

*Leaf division*.—Single.

*Leaf base*.—Cordate.

*Leaf apex*.—Acute and cuspidate.

*Leaf venation*.—Pinnate, color: young upper surface; N77A, young lower surface; N92A, upper mature surface; a blend of N92A and 202A, mature lower surface; N77A.

*Leaf margins*.—Entire and slightly undulate.

*Leaf attachment*.—Petiolate.

*Leaf arrangement*.—Single.

*Leaf surface*.—Upper surface and lower surface; coriaceous and glabrous.

*Leaf orientation*.—Held horizontal.

*Leaf color*.—Young foliage: upper surface; 137A suffused with N92A, lower surface; a blend of N77A and 137B to 137C, maturing foliage upper and lower surface becoming increasingly suffused with N92A, mature foliage upper surface; a blend of N92A and 202A with an overlay sheen of 98A, lower surface; N187A.

*Leaf size*.—Up to 66 cm in length and 48.8 cm in width.

*Leaf sinus*.—An average of 6.4 cm in depth on a mature leaf.

*Petioles*.—Held erect to semi-erect, an average of 91.4 cm in length and 6.3 mm in distal diameter and 2.5 mm in proximal diameter, glabrous and satiny surface, color; 187A, basal sheath portion is narrowly triangular in shape, an average of 2.5 mm in diameter and 9 cm in length, both surfaces; 187A in color, glabrous and satiny.

Inflorescence description:

*Blooming period*.—August to September in Eustis Fla.

*Inflorescence type*.—Spadix surrounded by a spathe, male portion held above female portion, only female flowers were developed.

*Inflorescence size*.—Average of 21.2 cm in length and 8 mm in width.

*Inflorescence bud*.—Linear to slightly narrow oblanceolate in shape, glabrous and smooth surface, an average of 21.2 cm in length, male portion; 8 mm in width, female portion; 1.3 cm in width, male portion; N187A in color and female portion; a blend of N187A and N77A.

*Flower fragrance*.—None.

*Lastingness of inflorescence*.—Inflorescence blooms intermittently during the bloom period, individual flowers last about 2 to 3 weeks.

*Inflorescence/flower quantity*.—Intermittent throughout the bloom season, sets of 3 or more, an average of 170 female flowers per spadix, male flowers were undeveloped.

*Spathe*.—Hooded, bract, subtending spadix, elliptic in shape, entire margin, acute apex, 15 cm in length and 8 mm in width, inner surface; coriaceous and smooth, outer surface; coriaceous and textured with linear grooves, lasts 5 to 7 days, color: when opening and fully open on inner rear surface 59A and outer rear surface; a blend of N187A and 187A.

*Spadix*.—Male portion above female zone, upright cylindrical shape (phallus-like), apex narrowly pointed, about 5 mm in diameter (not including ovary) and 8.3 cm in length, male zone; 5 mm in diameter and 5.4 cm in length, color immature and mature; a blend of N77 and 162A to 162B with 162A at the tip, female zone; 9 mm in diameter and 2.7 length, color immature and mature 144B with N92A at the tips.

*Peduncle*.—Triangular in shape, grows from base of plant, up to 30.5 cm in length and 6 mm in diameter, durable and strong, a blend of 187A and N187A in color, glabrous surface.

Reproductive organs:

*Gynoecium*.—1 pistil, 4 stigmas are N92A in color, ovary is flattened rotund in shape and 144B in color.

*Androcoecium*.—Undeveloped.

*Fruit and seed*.—Sterile.

It is claimed:

1. A new and distinct cultivar of *Colocasia* plant named 'Electric Blue Gecko' as herein illustrated and described.

* * * * *